US006302574B1

(12) United States Patent  (10) Patent No.: US 6,302,574 B1
Chan                      (45) Date of Patent:     Oct. 16, 2001

(54) PREPACKAGED LIQUID BONE CEMENT DISPENSER

(76) Inventor: Kwan-Ho Chan, 4803 First Pl., Lubbock, TX (US) 79416

( * ) Notice: Subject to any disclaimer, the term of this patent is extended or adjusted under 35 U.S.C. 154(b) by 0 days.

(21) Appl. No.: 09/172,932

(22) Filed: Oct. 14, 1998

Related U.S. Application Data

(62) Division of application No. 08/467,619, filed on Jun. 6, 1995.

(51) Int. Cl.[7] .......................... A61M 37/00; B67D 5/42; B01F 15/02
(52) U.S. Cl. ...................... 366/160.4; 366/162.1; 366/189; 366/267; 366/336; 222/137; 604/89
(58) Field of Search .................... 366/160.1, 177.1, 366/262, 181.5, 181.6, 189, 190, 162.1, 160.4, 267, 184, 332, 336, 339; 222/137, 145.1, 325; 206/219; 406/416; 604/89, 82

(56) References Cited

U.S. PATENT DOCUMENTS

| 3,144,966 | 8/1964 | Cook | 222/136 |
|---|---|---|---|
| 3,153,531 | 10/1964 | Cook | 259/113 |
| 3,223,083 | 12/1965 | Cobey | 128/92 |
| 3,390,814 | * 7/1968 | Creighton, Jr. et al. | 222/137 |

(List continued on next page.)

FOREIGN PATENT DOCUMENTS

| 0319639 | 6/1989 | (EP) . |
|---|---|---|
| 0380867 | 8/1990 | (EP) . |
| 0397589 | 11/1990 | (EP) . |
| 0528447 | 2/1993 | (EP) . |
| 2629337 | 10/1989 | (FR) . |
| WO9416951 | 8/1994 | (WO) . |
| WO9429012 | 12/1994 | (WO) . |

OTHER PUBLICATIONS

McGinnis et al., "Hand–Held Dispensing Equipment Reduces Waste and Saves Costs", *Adhesives Age*, Oct. 1991.
Brochure entitled "The Semkit® Package", Sep. 1991.

Primary Examiner—Tony G. Soohoo
(74) Attorney, Agent, or Firm—Sidley Austin Brown & Wood

(57) ABSTRACT

A fluid mixture dispenser has a container with independent fluid chambers that respectively maintain fluid components for combination. Each chamber includes an outlet and a driver. For each chamber, actuation of the driver effects the discharge of the fluid component through its outlet. The outlets of the fluid chambers open into a second container to receive a fluid mixture consisting of the fluid components, where the second container also includes an outlet and a driver. Actuation of the driver for the second container effects the discharge of the fluid mixture.

20 Claims, 6 Drawing Sheets

U.S. PATENT DOCUMENTS

| | | | |
|---|---|---|---|
| 3,489,147 | * 1/1970 | Shaw | 222/137 |
| 3,926,906 | 12/1975 | Lee, II et al. | 260/42.53 |
| 4,107,845 | 8/1978 | Lee, Jr. et al. | 32/15 |
| 4,182,035 | 1/1980 | Yamauchi et al. | 433/228 |
| 4,288,355 | 9/1981 | Anderson et al. | 260/29.6 M |
| 4,308,190 | 12/1981 | Walkowiak et al. | 260/29.7 UA |
| 4,383,826 | 5/1983 | Butler et al. | 433/228 |
| 4,477,604 | 10/1984 | Oechsle, III | 523/116 |
| 4,535,102 | 8/1985 | Kusumoto et al. | 523/116 |
| 4,538,920 | 9/1985 | Drake | 366/177 |
| 4,554,686 | 11/1985 | Baker | 623/16 |
| 4,626,310 | 12/1986 | Ritter | 156/307.3 |
| 4,722,948 | 2/1988 | Sanderson | 523/115 |
| 4,767,026 | 8/1988 | Keller et al. | 222/137 |
| 4,776,704 | * 10/1988 | Kopunek et al. | 366/184 |
| 4,886,843 | 12/1989 | Walton | 522/174 |
| 4,889,432 | * 12/1989 | Patterson | 366/177.1 |
| 4,952,068 | * 8/1990 | Flint | 366/337 |
| 4,969,747 | 11/1990 | Colin et al. | 366/339 |
| 4,973,168 | 11/1990 | Chan | 366/139 |
| 4,975,028 | 12/1990 | Schultz | 417/442 |
| 4,986,443 | * 1/1991 | Saur et al. | 222/137 |
| 5,033,650 | 7/1991 | Colin et al. | 222/137 |
| 5,080,262 | 1/1992 | Herold et al. | 222/135 |
| 5,100,241 | 3/1992 | Chan | 366/139 |
| 5,266,608 | 11/1993 | Katz et al. | 523/111 |
| 5,279,550 | 1/1994 | Habib et al. | 604/38 |
| 5,338,773 | 8/1994 | Lu et al. | 523/116 |
| 5,370,221 | 12/1994 | Magnusson et al. | 206/221 |
| 5,443,182 | * 8/1995 | Tanaka et al. | 222/137 |

\* cited by examiner

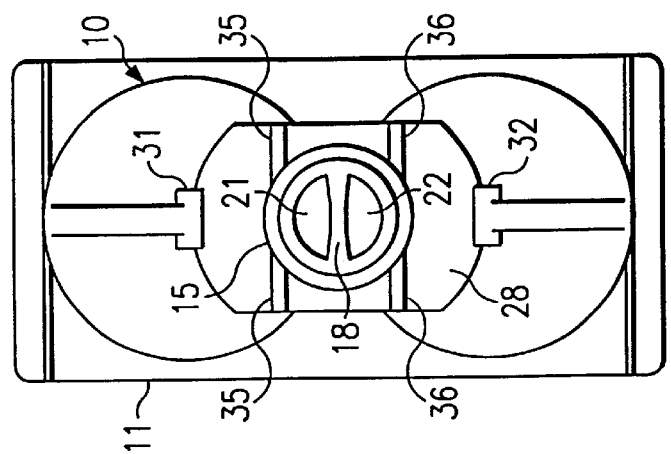
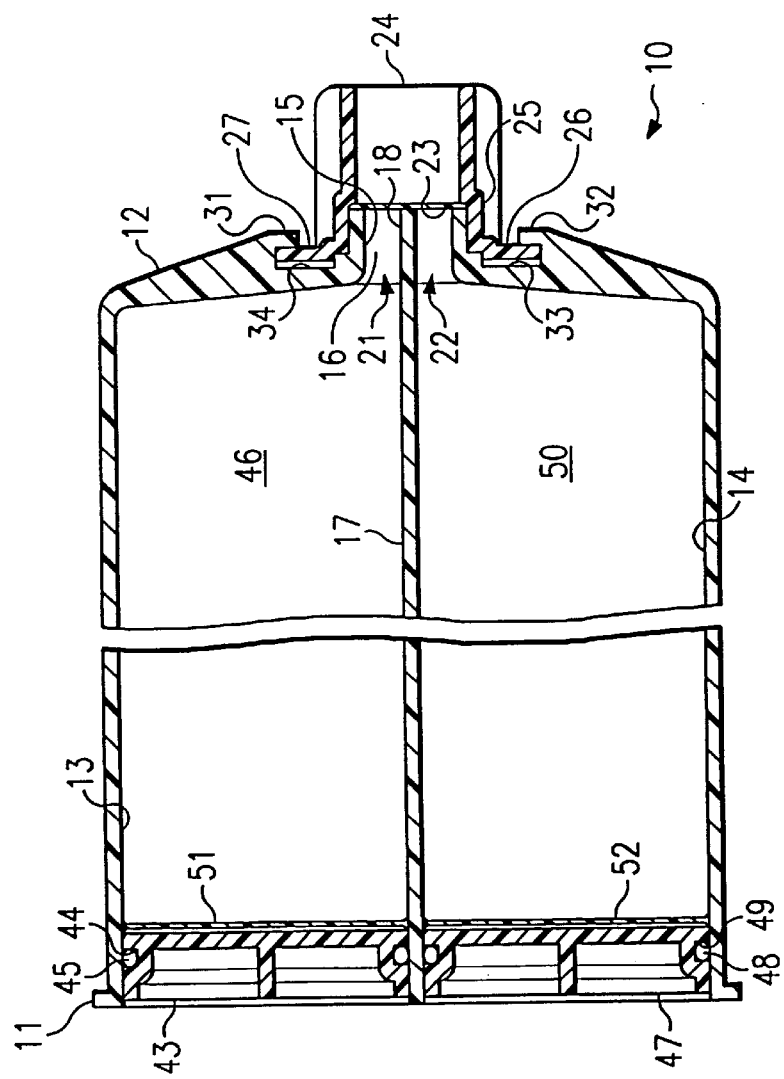

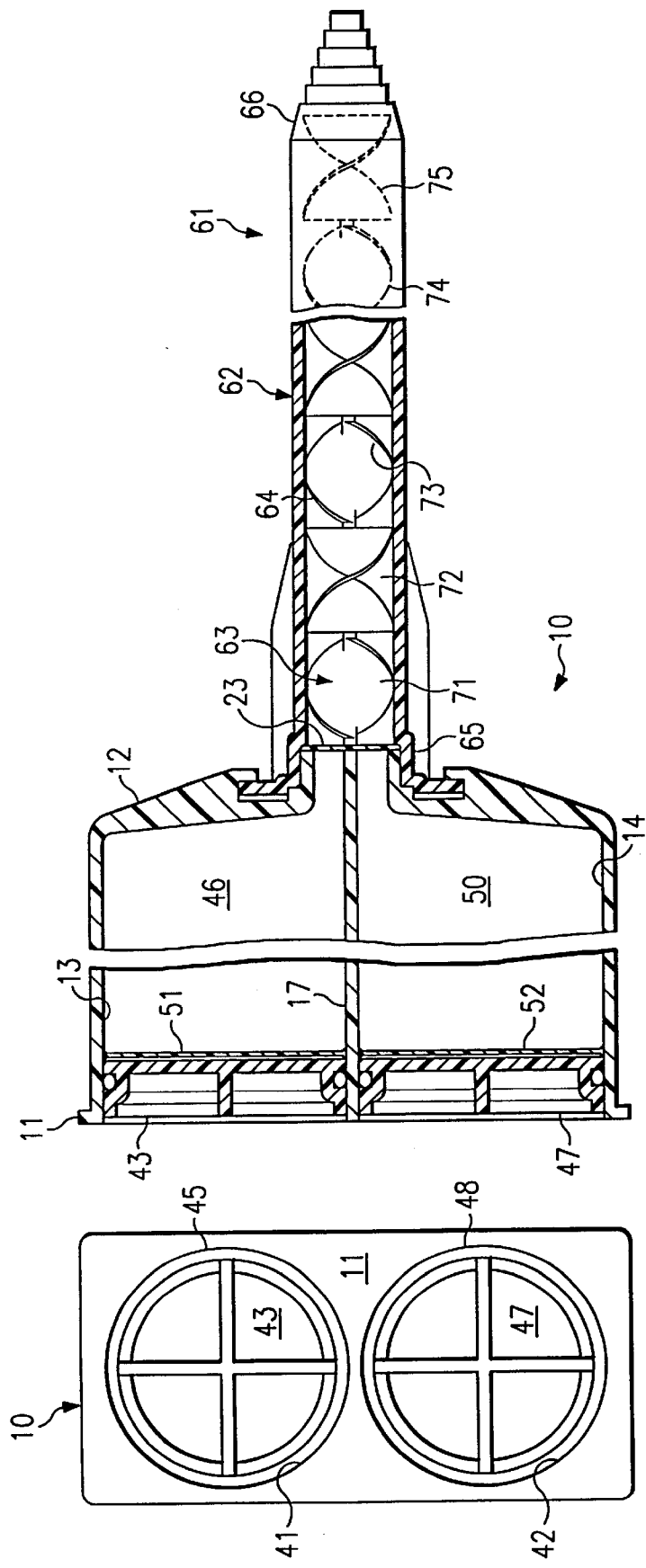

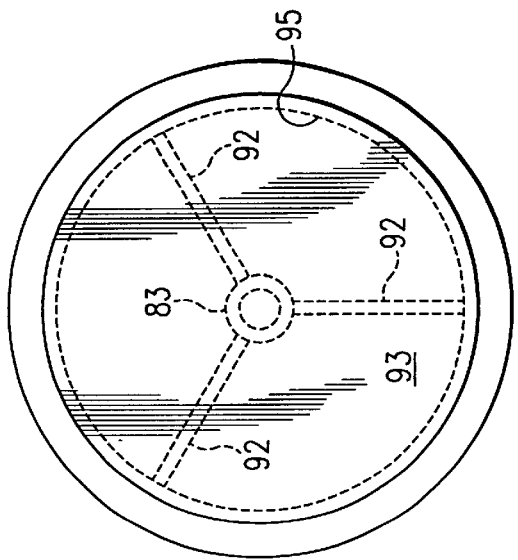
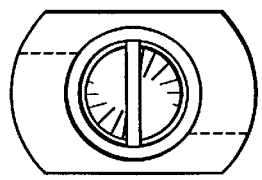
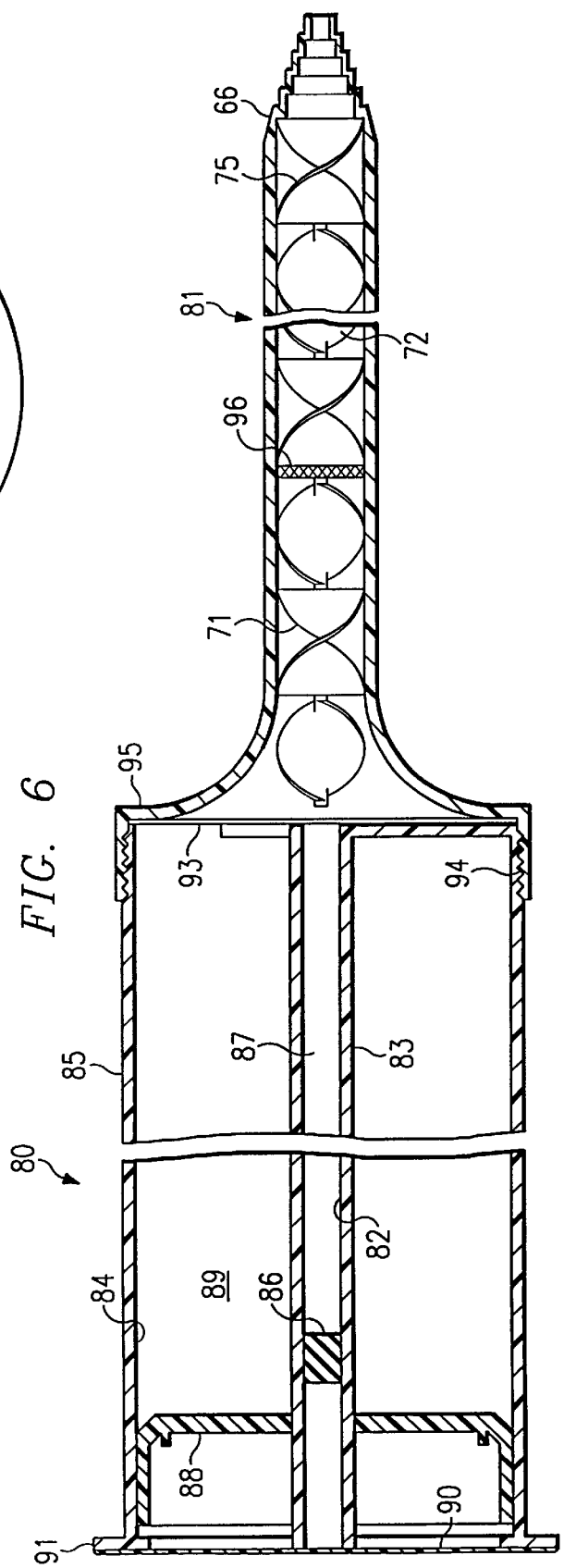
FIG. 5
FIG. 7
FIG. 6

PREPACKAGED LIQUID BONE CEMENT DISPENSER

RELATED APPLICATIONS

This application is a divisional of Ser. No. 08/467,619, filed Jun. 6, 1995, now pending.

FIELD OF THE INVENTION

This invention relates to a container to dispense a fluid mixture, and in particular, to a multiple stage container to dispense a fluid mixture.

BACKGROUND OF THE INVENTION

Poly(methyl methacrylate) bone cement, which has been used routinely for the fixation of metallic or plastic implants in joint replacement surgery for about thirty years, is based on a monomer which can be admixed with a curing system and applied to the bone under conditions which permit the monomer to polymerize in situ in the bone. However, as the polymerization of methyl methacrylate is an exothermic reaction, resulting in the evolution of heat, it is desirable that the amount of monomer in the unset bone cement be minimized in order to avoid any damage to the bone tissue. One technique for minimizing the monomer concentration in the unset bone cement, while still achieving the benefits of the characteristics of the resulting poly(methyl methacrylate), is to include a substantial amount of small particles of the polymer in the unset bone cement composition, e.g., about 2 grams of polymer powder per milliliter of monomer. The size of the polymer powder particles is generally in the range of about 30 to about 150 $\mu m$ in diameter. As the polymerization of methyl methacrylate is accompanied by a substantial decrease in volume, the reduction in the amount of the monomer required in the bone cement by the inclusion of a large amount of poly(methyl methacrylate) powder also minimizes the shrinkage experienced during the setting of the bone cement. Thus, methyl methacrylate bone cement is most commonly available in two standard packages, one containing 40 mg. of poly (methyl methacrylate) powder and the other containing 20 ml of liquid methyl methacrylate monomer.

In order to effect the polymerization of the monomer, the bone cement composition also contains an initiator and an activator. Thus, poly(methyl methacrylate) bone cement has generally been formed by operating room personnel admixing a powdery component, containing the polymer powder and an initiator, and a liquid component, containing the liquid monomer and an activator, to obtain the unset cement, which must then be quickly applied to the bone, as the cement composition sets within a few minutes. For example, poly(methyl methacrylate) bone cement can be prepared by mixing together the following ingredients: liquid methyl methacrylate, powder particles of poly(methyl methacrylate), benzoyl peroxide powder as the polymerization initiator, and N,N-dimethyl-p-toluidine (DMPT) as an activator. Occasionally, a poly(methyl acrylate) or a polystyrene copolymer has also been included in the polymeric components for forming the bone cement.

As early as 1975 the importance of reducing the porosity of the set bone cement in order to improve the mechanical properties of the set bone cement was recognized. This porosity is a source of mechanical weakness of the cement material and can cause early failure of fixation of the implant. The porosity of set bone cement can be measured either as a volume percentage or as a percentage of cross-sectional area occupied by voids. Regardless of the method of measurement, the generally reported values for set bone cement, resulting from hand-mixed bone cement of regular viscosity, are in the range of about 5 to about 16 percent.

The porosity of set bone cement can be the result of the entrapment of air during the mixing and transferring process, the presence of air spaces between polymer particles at the time of the addition of the other components to the polymer particles, the generation of voids in the unset bone cement as a result of evaporation or boiling of the monomer during the mixing process or during the setting of the bone cement, the thermal expansion of existing bubbles, and the presence of cavitation voids. Of these causes, the most common source of porosity, as well as the most easily controlled, is air entrapment during the mixing and transferring process.

It is well known that vigorous hand mixing of bone cement components, under atmospheric conditions, increases the amount of air in the resulting bone cement mixture. Because of the viscous nature of the resulting bone cement mixture, only large bubbles, e.g., having a diameter greater than 1 cm, can easily migrate to the surface of the unset bone cement mixture, leaving a substantial number of voids in the bone cement mixture with a diameter of less than 1 cm.

When the powdery component and the liquid monomeric component are mixed, a doughy mixture is formed, and the initiator and activator in the mixture start polymerization of the liquid monomeric component. When mechanical agitation is employed during the mixing of the liquid and powder components, air can be trapped within the resulting doughy mixture. The entrapped air causes porosity in the resulting solidified cement mixture.

While porosity generally occurs throughout the body of polymerized bone cement as a result of the above listed causes, there are also regional variations, particularly in the cement mantle surrounding a femoral hip stem. Greater porosity is noted in the proximal cement mantle. In addition, the porosity is preferentially concentrated at the cement-prosthesis interface of a cemented femoral stem in a total hip replacement due to the rheological behavior of the bone cement during the implant insertion. The concentration of the porosity at the interface greatly exceeds the average porosity of the bulk cement. This interfacial concentration of porosity cannot be reduced by the prior centrifugation of the bone cement.

Considerable effort has been directed to reducing the amount of porosity in set bone cement, with centrifugation, vacuum mixing, and ultrasonic agitation of the unset bone cement mixture being the most frequently employed techniques. Currently, centrifugation and vacuum mixing are being used clinically. As an example, the prepackaging of the powdery component of the bone cement under high vacuum in a mixing vessel, which permits the addition of the liquid monomer component to the powder without the introduction of air into the vessel, thereby minimizing the presence of air bubbles in the resulting cement, is described in Chan, U.S. Pat. No. 4,973,168, and Chan, U.S. Pat. No. 5,100,241. However, the use by operating room personnel of either high vacuum mixing or centrifugation in the operating room can significantly complicate the procedure.

Storing liquid bone cement monomer in a non-glass container presents a major engineering and manufacturing challenge. The problem is even greater where the container has a sliding piston, as it is extremely difficult to achieve a hermetic seal with a sliding piston in the presence of liquid bone cement monomer.

Accordingly, it is desirable that a technique be found to provide a poly(alkyl methacrylate) bone cement kit which can be readily utilized in the operating room to prepare the poly(alkyl methacrylate) bone cement composition from only two prepackaged components without requiring either high vacuum mixing or centrifugation.

SUMMARY OF THE INVENTION

In accordance with the present invention, the poly(alkyl methacrylate) bone cement ingredients are prepackaged as two separate components where both components are in a liquid form that is at least substantially air-free. The first liquid component is formed by premixing a bone cement liquid monomer with bone cement polymer powder and a polymerization initiator to form a liquid mixture. A stabilizer is included in the first liquid component to prevent spontaneous polymerization of the monomer contained in the first liquid component. The second liquid component is formed by premixing bone cement liquid monomer with bone cement polymer powder, if any, and an activator to form a liquid mixture. A stabilizer is also included in the second liquid component to prevent spontaneous polymerization of the monomer contained in the second liquid component. The monomer/polymer ratio of each liquid component containing polymer will be in the range from the minimum required to provide the respective component as a liquid mixture up to the maximum which, when the two liquid components are mixed, will result in the desired monomer/polymer ratio for the mixture.

In use, the two liquid bone cement components are prepackaged in two separate chambers of a container. The container can be used with a mixer that can properly mix the two liquid components without mechanical agitation and without the introduction of air into the two liquid components during the transfer of the two liquid components from their separate chambers to the mixer and during mixing. In a presently preferred embodiment, a static mixer can be incorporated within a disposable dispensing nozzle which is included in a kit along with a disposable container having two separate chambers, each being filled with a respective one of the liquid bone cement components.

In another aspect of the preferred embodiment, the disposable dispensing nozzle couples the two separate chambers of the container to a second dispensing container. The second container receives the two liquid components to allow, for example, some selected degree of polymerization prior to dispensing the mixture to a selected site.

BRIEF DESCRIPTION OF THE DRAWINGS

FIG. 1 is a cross-sectional view along the longitudinal axis of a side-by-side dual cylinder package of bone cement components in accordance with a first embodiment of the present invention, having a protector cap in place;

FIG. 2 is a view of the outlet end of the package of FIG. 1, with the protector cap being omitted;

FIG. 3 is a view of the piston end of the package of FIG. 1;

FIG. 4 is a cross-sectional view along the longitudinal axis of the package of FIG. 1 with the protector cap being replaced by a static mixer;

FIG. 5 is a view of the inlet end of the static mixer of FIG. 4;

FIG. 6 is a cross-sectional view along the longitudinal axis of concentric cylinders package of bone cement components in accordance with a third embodiment of the present invention, having a static mixer in place;

FIG. 7 is a view of the outlet end of the package of FIG. 8 with the static mixer being omitted;

DETAILED DESCRIPTION

Figure 8:
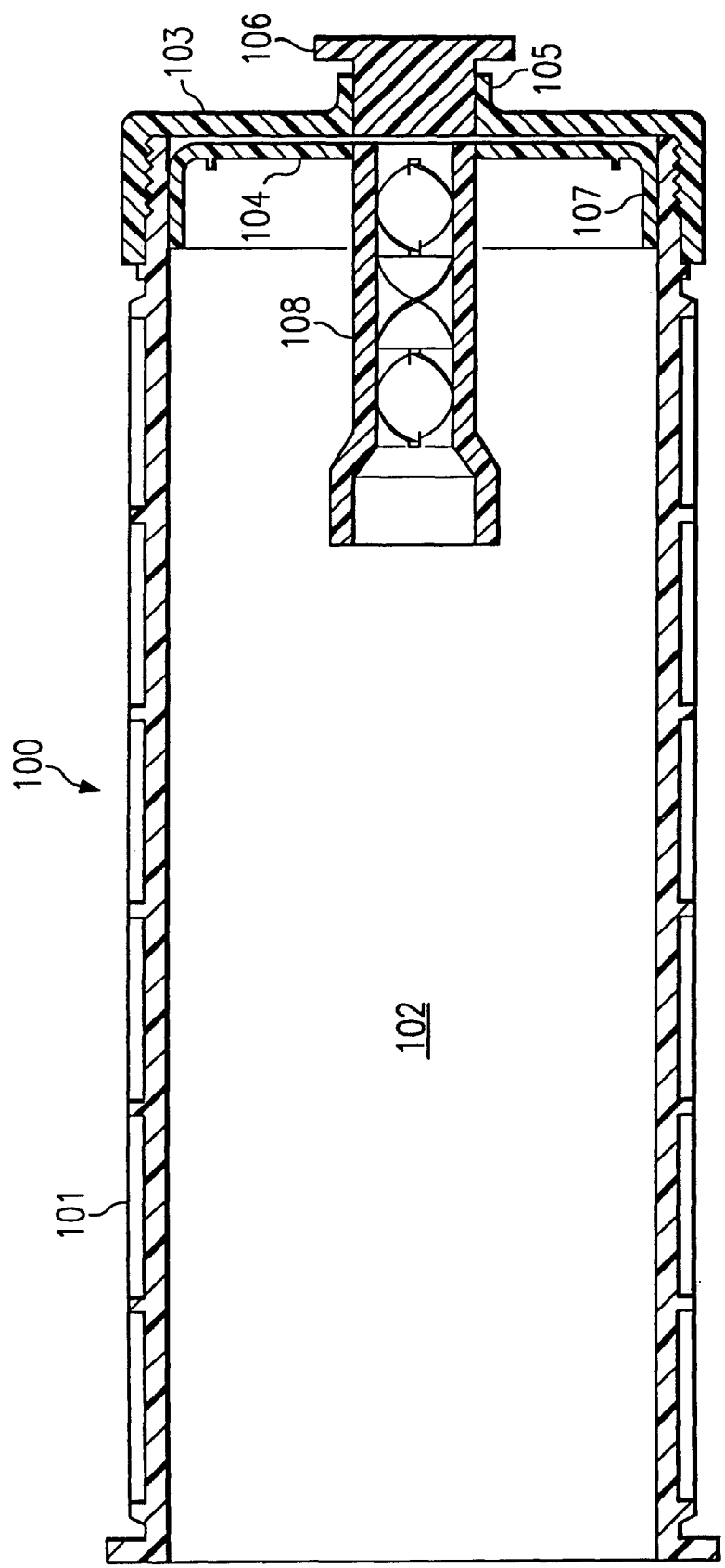
FIG. 8 is a cross-sectional view along the longitudinal axis of a "holding" cartridge, having a protector cap in the opening in the outlet end and containing a piston with a static mixer in communication with the chamber between the piston and the outlet end.

The term "liquid", as used herein, indicates a material having a definite volume but without a definite shape except such as is temporarily given by a container and which is readily lost by the material flowing under the application of moderate stress. Thus, while the term "liquid" includes a range of materials from those which flow freely like water to those which can be characterized as paste-like or doughy, all of such materials can be readily extruded from a container.

In accordance with the present invention, the bone cement ingredients are prepared in the form of two separate components, with each component being in a liquid form and at least substantially air-free, and with each liquid component comprising a bone cement liquid monomer and at least one of the liquid components containing dispersed therein a bone cement polymer which was in powder form prior to the inclusion in the respective liquid component. Each liquid component is packaged in a separate chamber of a dual compartment container so as to be air-free. A static mixer can be attached to the container so as to receive the two components as they are extruded from their respective chambers. The static mixer mixes the two liquid components as they pass through the static mixer without requiring mechanical agitation and without the introduction of air into the liquid mixture.

In most instances, the bone cement polymer powder will be dissolved in the bone cement liquid monomer. However, due to either the type or the amount of the bone cement polymer, it is possible for at least some of the bone cement polymer powder to be dispersed in the liquid monomer without dissolving in the liquid monomer.

A suitable dual compartment container 10, which is illustrated in FIG. 1, has a piston end wall 11 and an outlet end wall 12. The container 10 has two cylindrical compartments 13 and 14, each of which extends from the inner surface of the outlet end wall 12 to a respective opening in the piston end wall 11, such that the longitudinal axes of the compartments 13 and 14 are parallel to each other and to the longitudinal axis of container 10. The outlet end wall 12 has a centrally located annular wall 15 extending outwardly therefrom in a direction parallel to the longitudinal axes of compartments 13 and 14 to form an outlet compartment 16. A common wall 17 separates compartments 13 and 14 from each other, and a portion 18 of the common wall 17 extends into and through outlet compartment 16 so that the outermost end surface of the portion 18 is coplanar with the outermost end surface of the annular wall 15. The portion 18 of the common wall 17 divides the outlet compartment 16 into a first outlet passageway 21 which is in fluid communication with compartment 13, and a second outlet passageway 22 which is in fluid communication with compartment 14.

In a presently preferred version of this container 10, the outlet ends of outlet compartments 21 and 22 are sealed by a thin, air impermeable layer 23. The layer 23 is bonded to the outermost end surface of portion 18 of the common wall 17 and to the circumferential periphery of the annular wall 15 to form an air tight seal for each of the outlet ends of outlet passageways 21 and 22. The sealing layer 23 can be formed of any suitable material and be bonded by any suitable means, e.g., a thin metal foil having an adhesive coating thereon. However, a thermoplastic material, e.g., polyethylene, polypropylene, poly(4-methyl-1-pentene), a copolymer of ethylene and another 1-olefin, etc., is advantageous for forming the sealing layer 23 because of the ease of achieving a thermal bond or an ultrasonic bond between the sealing layer 23 and the surfaces of the annular wall 15 and the end portion 18 of the common wall 17.

Due to the desired thinness of sealing layer 23, it is desirable to apply a protector cap 24 over the sealing layer 23 to protect the sealing layer 23 against unintended rupture thereof. The protector cap 24 can be provided with an annular skirt 25 and discontinuous arcuate segment flanges 26 and 27 located on opposite sides of the distal end of skirt 25. The skirt 25 has a frustoconical inner surface which corresponds to the frustoconical outer surface of the annular wall 15 so that these two surfaces mate when the protector cap 24 is in place on the annular wall 15.

Referring to FIGS. 1 and 2, the outlet end wall 12 of container 10 can be provided with an outer planar surface 28, which is generally perpendicular to the longitudinal axis of container 10, and with two radially inwardly directed flanges 31 and 32 which overlie portions of planar surface 28 on opposite sides of the periphery of the annular wall 15 so as to form two radially inward opening slots 33 and 34. The maximum diameter of the cap skirt 25, excluding the arcuate flanges 26 and 27, is less than the diameter of the opening between the inner edges of end flanges 31 and 32, while the maximum diameter of the cap flanges 26 and 27 is greater than the opening between the inner edges of end flanges 31 and 32 but less than the diameter represented by the radially outer ends of the slots 33 and 34. The thickness of each of the cap flanges 26 and 27 is only slightly less than the dimension of the slots 33 and 34 which is parallel to the longitudinal axis of the container 10. Outwardly extending ridges 35 and 36 can be provided on planar surface 28 so as to extend at least generally perpendicular to a line extending from slot 33 to slot 34 so that the protector cap 24 can be initially placed coaxially on the annular wall 15 and in contact with the ridges 35 and 36, with a line extending from the arcuate flange 26 to the arcuate flange 27 being substantially perpendicular to the line extending from slot 33 to slot 34, and then the protector cap 24 can be rotated approximately 90° so that each of the arcuate flanges 26 and 27 enters a respective one of the slots 33 and 34 to enable the inwardly directed flanges 31 and 32 to hold the protector cap 24 against the ridges 35 and 36, thereby locking the protector cap 24 in place.

Referring to FIGS. 1 and 3, the piston end wall 11 of the container 10 has two circular openings 41 and 42 formed therein, representing the open ends of compartments 13 and 14. A circular piston 43 is positioned in compartment 13 coaxially therewith. An annular outer wall of the piston 43 is provided with an annular groove 44 containing an O-ring 45 such that the O-ring 45 is in radial compression between the piston 43 and the annular inner wall of compartment 13. Thus, piston 43, O-ring 45, and the compartment 13 define a first chamber 46 extending from the piston 43 to the inner surface of the outlet end wall 12. A similar circular piston 47 is positioned coaxially in compartment 14, with an O-ring 48 being positioned in an annular groove 49 in the annular outer wall of the piston 47 so as to be in radial compression between the piston 47 and the annular inner wall of compartment 14. Thus, piston 47, O-ring 48, and the compartment 14 define a second chamber 50 extending from the piston 47 to the inner surface of the outlet end wall 12. In the illustrated embodiment, the chambers 46 and 50 have the same diameter and the same volume. However, if desired, the two chambers can be provided with different diameters and different volumes. Suitable containers include the Cartridge System 50 and Cartridge System 400 dual chamber containers, available from ConProTec Inc., 6 Raymond Avenue, Salem, N.H., in 1:1, 2:1, 4:1, and 10:1 volume ratios for the two chambers.

Liquid bone cement monomer can be successfully stored in polyethylene cartridges or flexible polyethylene bags. However, the presence of sliding pistons 43 and 47 represents a potential problem as it is extremely difficult to achieve a hermetic seal with a sliding piston in the presence of liquid bone cement monomer. In the illustrated version of the container 10, the piston ends of chambers 46 and 50 are sealed by thin, air impermeable layers 51 and 52, respectively. The peripheral edge of sealing layer 51 is bonded either to the inner surface of the compartment 13 or to the outer surface of the piston end wall 11 of the container 10 to form an air tight seal with the piston 43 being separated from the contents of chamber 46 by the sealing layer 51. Similarly, the peripheral edge of the sealing layer 52 is bonded either to the inner surface of the compartment 14 or to the outer surface of the piston end wall 11 of the container 10 to form an air tight seal with the piston 47 being separated from the contents of chamber 50 by the sealing layer 52. Sealing layers 51 and 52 can be formed of the same material as sealing layer 23 at the outlet end wall 12 of the container 10. The sealing layers 23, 51, and 52 assist in maintaining sterile conditions for the contents of chambers 46 and 50 prior to use of the bone cement components, and an examination of these sealing layers prior to the dispensing of the contents of the chambers 46 and 50 can serve to indicate whether any unintended rupturing of these sealing layers has occurred, thereby placing the sterile conditions in question.

Thus, sealing layers 23, 51 and 52 provide a hermetic seal for the liquid bone cement monomer from the time of preparation of the filled container until the time of preparation of the bone cement. In one method of fabricating the filled container 10, a thin polyethylene membrane 23 is lightly welded to the exterior surface of the outlet wall 15 of the container 10 so as to allow easy rupture when sufficient pressure is generated in the liquid component chambers 46 and 50 by the advancing pistons. After the introduction of the liquid components into the chambers 46 and 50, the chambers 46 and 50 can be sealed at the piston end by thin polyethylene membranes 51 and 52 which are ultrasonically welded to the surfaces of the container 10. Each of the pistons 43 and 47 is then inserted at the piston end of the container 10 over the polyethylene membrane 51 or 52. The force of the dispenser plunger on the container piston should be large enough to rupture the thin polyethylene membrane 51 or 52, allowing the piston 43 or 47 to slide forward.

Referring now to FIGS. 4 and 5, the protector cap 24 has been removed from the container 10 and replaced by a mixer-dispenser 61. The mixer-dispenser 61 has a housing 62 and a static mixer 63. The housing 62 comprises an annular intermediate section 64, an inlet end section 65, and a nozzle section 66, each being of generally circular cross-section perpendicular to the longitudinal axis of housing 62. The inlet end section 65 has an internal annular surface corresponding to the outer annular surface of wall 15 of the container 10 so that these surfaces mate when the mixer-dispenser 61 is mounted on the container 10. The inlet end section 65 has discontinuous arcuate segmental flanges 67 and 68 on opposite sides of the distal end of the inlet end section 65 as illustrated in FIG. 5. Thus, the arcuate flanges 67 and 68 are of the same shape and size as the arcuate flanges 26 and 27 on the protector cap 24, and function in the same manner to engage flanges 31 and 32 to secure the mixer-dispenser 61 to the container 10. As shown in FIG. 4, although the protector cap 24 has been removed and the mixer-dispenser 61 has been mounted on the container 10, the sealing layer 23 is still in place.

The static mixer 63 comprises a plurality of static mixing vanes 71–75 consecutively positioned along the longitudinal axis of the housing 62, with alternating right hand and left hand twists. Each static mixing vane 71–75 is in the form of a ribbon which is rotated in one direction about its longitudinal centerline so as to form two flow paths of at least substantially equal cross-section on opposite sides of the ribbon. While five static mixing vanes have been illustrated, any suitable number can be employed which is effective to achieve the desired degree of mixing of the two liquid components. Each end of a static mixing vane, other than the outer end of each of the two end static mixing vanes, is positioned approximately 90° to the adjacent end of a neighboring static mixing vane. The upstream end of the first static mixing vane 71 is positioned approximately 90° to the wall portion 18. For simplicity in the assembling of the static mixing vanes 71–75 in the mixer-dispenser 61, the static mixing vanes 71–75 are preferably formed as a single molding which can be inserted into the intermediate section 64 via the inlet end section 65. However, it is also possible to form the static mixing vanes as two or more sections which can be sequentially inserted into the intermediate section 64. Although the mixer-dispenser 61 normally contains air at atmospheric pressure at the time the mixer-dispenser 61 is connected to the outlet of the container 10, the small internal diameter of the intermediate section 62 results in only a small area of contact of the liquid components and the air as the advancing liquid mixture moves the air out of the mixer-dispenser. Thus, the liquid mixture exiting the nozzle 66 is at least substantially free of air, and the presence of air bubbles in the resulting set bone cement is minimized or eliminated.

The nozzle end section 66 can be in the form of a frustoconically shaped annular member or in the form, illustrated in FIG. 4, of a series of annular sections of circular cross-section with diameters thereof decreasing toward the tip of the nozzle end section 66. In either case, the tip of the nozzle end section can be severed to provide an outlet opening of the desired cross-section. Suitable static mixer-dispensers are the STATOMIX® MA static mixers available from ConProTec Inc., 6 Raymond Avenue, Salem, N.H.

At the time of the preparation of the bone cement, the protector cap 24 is removed from the dual chamber container 10, the mixer-dispenser 61 is then attached to the outlet of the dual chamber container 10, the tip of the nozzle end section 66 is severed, either before or after the mixer-dispenser 61 is attached to the dual chamber container 10, and the dual chamber container 10 is inserted into a dispensing device having two plungers for engaging the pistons 43 and 47. The dispensing device can have any suitable mechanism, e.g., manual or pneumatic, for simultaneously driving the pistons forwardly at the same rate of movement. Suitable dispensing devices are the MIXPAC® DP-400-85 pneumatic dispensers and the MIXPAC® DM-400 manual dispensers, available from ConProTec Inc., 6 Raymond Avenue, Salem, N.H. The plungers contact the back side of the pistons 43 and 47 and upon actuation of the dispensing device, simultaneously move the pistons 43 and 47 forwardly at the same rate, rupturing the sealing layers 23, 51, and 52, reducing the volumes of the chambers 46 and 50, and thereby extruding the two liquid components in the chambers 46 and 50 through the respective outlet passageways 21, 22 and into the inlet end of the static mixer 63. At the upstream end of the static mixing vane 71, each liquid component is divided into two approximately equal streams, with each of the two streams of one component entering a respective one of the two flow paths through the first static mixing vane 71, along with one of the two streams of the other liquid component. At each junction of two static mixing vanes in the static mixer 63, each liquid flow from the upstream static mixing vane is split into two parts with each of these two parts entering a different one of the two flow paths in the downstream static mixing vane along with one of the two parts of the other liquid flow from the upstream static mixing vane. Thus, the two liquid components from chambers 46 and 50 are mixed together by the static mixer 63 without mechanical agitation and without introducing air into the liquid mixture.

A kit for the first embodiment comprises the mixer-dispenser 61 and the container 10, with the chamber 46 filled with a first liquid bone cement component, the chamber 50 filled with a second liquid bone cement component, and the protector cap 24 and the pistons 43 and 47 in place. Each of the structural components of the dual chamber container 10, other than the O-rings 45 and 48, and each of the structural components of the mixer-dispenser 61 are advantageously formed of a thermoplastic material such as polyethylene, polypropylene, poly(4-methyl-1-pentene), a copolymer of ethylene and another 1-olefin, nylon, polyacetal, etc., so that after the bone cement components are mixed and dispensed, the container 10 and the mixer-dispenser 61 can be thrown away. The dispensing device can also be disposable, but is preferably formed of materials which can be sterilized and reused in an operating room environment.

If desired, a single thin, air impermeable layer can be bonded to the exterior surface of piston end wall 11 of the dual chamber container 10 to provide a seal, instead of the two sealing layers 51 and 52 illustrated in FIG. 1. Such a single layer would protect against the possibility of any contaminants entering the small gap between the periphery of the pistons 43 and 47 and the adjacent compartment sidewall, as well as readily permitting a visual inspection for any rupture in the single layer.

While the sealing layers 23, 51, and 52 have been illustrated as single layers, it is possible to fabricate one or more of these seals in the form of two opposing films, with each film having a first portion bonded to the container structure and a second, flap portion lightly bonded to the second, flap portion of the opposing film, such that upon pressurization of the respective seal, the two flap portions are separated from each other.

A second embodiment of a suitable dual compartment container 80 is illustrated in FIGS. 6 and 7 with a mixer-dispenser 81 in place. The components of the mixer-dispenser 81 which are the same as in the mixer-dispenser 61 of FIG. 1 are given the same reference numerals and the detailed description thereof will be omitted. The container 80 has a cylindrical first compartment 82 within the annular member 83 and an annular second compartment 84 between the annular member 83 and the annular housing 85, which is positioned coaxially with and exteriorly of the annular member 83. A cylindrical first piston 86 is positioned within compartment 82 to form a first chamber 87 between the piston 86 and the outlet end of the container 80, while an annular second piston 88 is positioned in compartment 84 to form a second chamber 89 between the piston 88 and the outlet end of the container 80. A single thin, air impermeable layer 90 is bonded to the exterior surface of the piston end wall 91 of the container 80 and the exterior end of the annular member 82 so as to provide a seal for both compartments 82 and 84. In the illustrated embodiment, the chambers 87 and 89 have different cross-sectional areas and different volumes. However, if desired, the two chambers can be provided with equal cross-sectional areas and equal volumes.

The piston end of the annular member 83 is supported coaxially in the housing 85 by the piston 88. The outlet end portion of the annular member 83 is supported coaxially in the housing 85 by three fixed struts 92, which are spaced apart at approximately 120° intervals in a plane perpendicular to the longitudinal axis of the housing 85 and which extend between the annular member 83 and the housing 85. The outlet end of each of the inner chamber 87 and the outer chamber 89 is sealed by a single thin, air impermeable layer 93 bonded to the outlet end of the housing 85 and the annular member 83. The outlet end portion 94 of the housing 85 is provided with external threads, while the inlet end portion 95 of mixer-dispenser 81 is provided with matching internal threads so that the inlet end portion 95 of mixer-dispenser 81 serves as a protector cap for the sealing layer 93. If desired, a separate protector cap can be provided to protect the outlet end of the container 80 until time to prepare the bone cement, at which time the separate cap would be removed and replaced by the mixer-dispenser 81. If desired, a screen 96 can be placed at each junction of two adjacent static mixing vanes in order to enhance the mixing of the two liquid flows entering the respective junction. The containers are connected to a common nozzle. The two pistons are advanced simultaneously, forcing the right proportion of each liquid component into the common mixer-dispenser 81. The spiral fins within the proximal part of the mixer-dispenser 81 mix the liquid components by laminar shear, while the screens 96 break up the laminar flow and mix the liquid components further by turbulence.

A kit for the second embodiment comprises the mixer-dispenser 81 and the container 80, with the chamber 89 filled with a first liquid bone cement component, the chamber 87 filled with a second liquid bone cement component, and the pistons 86 and 88 and the sealing layers 90 and 93 in place. If desired, the container 80 can be provided with a protective cap over the outlet end, with the mixer-dispenser 81 being a separate item in the kit. Each of the structural components of the dual chamber container 80 and each of the structural components of the mixer-dispenser 81 are advantageously formed of a thermoplastic material such as polyethylene, polypropylene, poly(4-methyl-1-pentene), a copolymer of ethylene and another 1-olefin, etc., so that after the bone cement components are mixed and dispensed, the container 80 and the mixer-dispenser 81 can be thrown away. As with the first embodiment, the dispensing device can also be disposable, but is preferably formed of materials which can be sterilized and reused in an operating room environment.

At the time of the preparation of the bone cement, the tip of the nozzle end section 66 is severed, and the concentric chambered container 80 is inserted into a dispensing device having two concentric plungers for engaging the pistons 86 and 88, thereby rupturing the sealing layer 90. The dispensing device can have a manual mechanism or a pneumatic mechanism for simultaneously driving the pistons forwardly at the same rate of movement. The plungers contact the back side of the pistons 86 and 88 and upon actuation of the dispensing device, simultaneously move the pistons 86 and 88 forwardly at the same rate, rupturing the sealing layer 93, reducing the volumes of the chambers 87 and 89, and thereby extruding the two liquid components in the chambers 87 and 89 into the inlet end of the static mixer 81. The upstream end of static mixing vane 71 is positioned adjacent the outlet end of annular member 83 so that each of the liquid components is divided into two approximately equal streams, with each of the two streams of one component entering a respective one of the two flow paths through the first static mixing vane 71, along with one of the two streams of the other liquid component. At each junction of the two static mixing vanes in the static mixer 81, each liquid flow from the upstream static mixing vane is divided into many small streams by the screen 96, thereby enhancing the mixing. Again, the mixing of the two liquid components is achieved without mechanical agitation and without the introduction of air into the liquid mixture.

While the invention has been illustrated in terms of the preferred use of a static mixer-dispenser, any suitable static mixer or dynamic mixer can be employed, e.g., a dashpot mixer, etc. The dashpot mixer offers an advantage to the surgeon who prefers that the monomer in the bone cement mixture undergo at least some degree of polymerization prior to the introduction of the bone cement into the bone site, in that the surgeon can determine the period of time between the introduction of the two components into the mixer and the ejection of the partially polymerized mixture from the mixer into the bone site. This partial polymerization can also be achieved by dispensing the mixed components onto a sanitary surface such as a plastic bowl, and subsequently removing from the sanitary surface a desired amount of the bone cement mixture which has achieved the desired state of partial polymerization.

Figure 9:
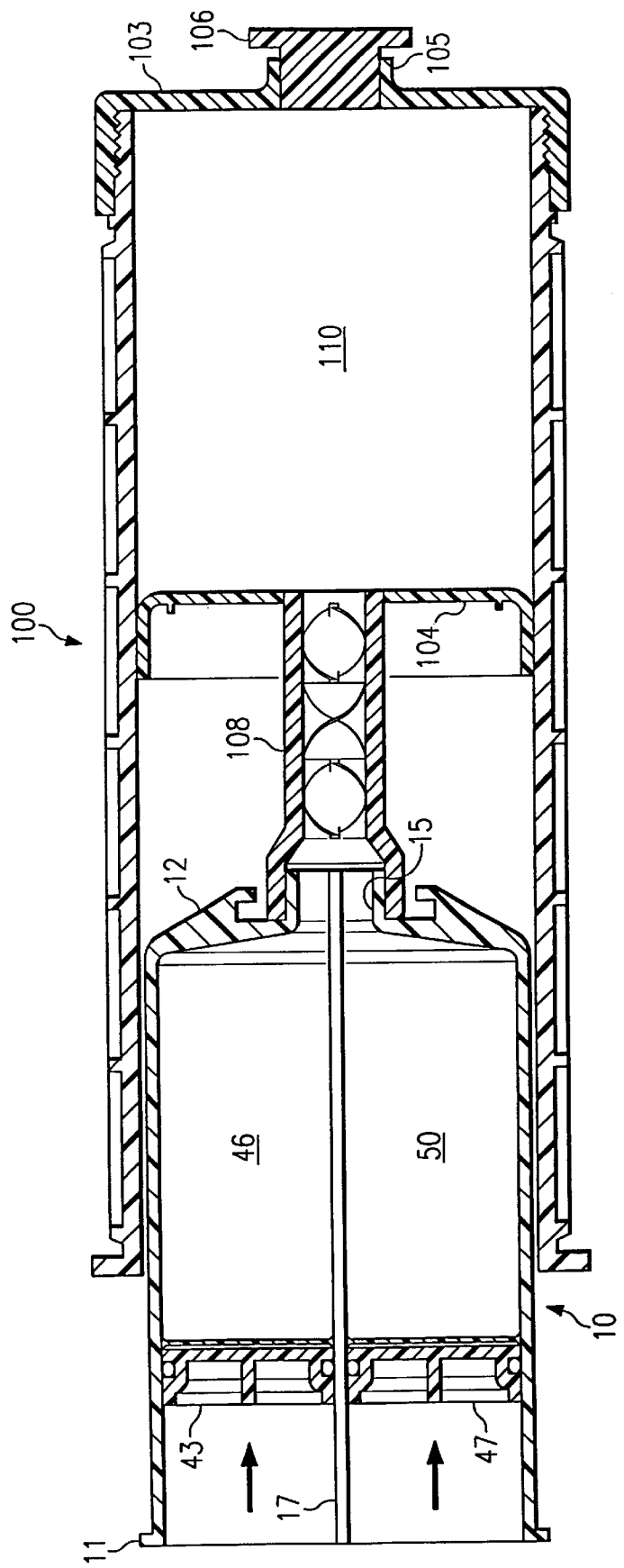
FIG. 9 is a cross-sectional view along the longitudinal axis of the "holding" cartridge of FIG. 8 with the container of FIG. 4 inserted into the open end of the "holding" cartridge and connected to the static mixer, for transferring the contents of the container into the chamber of the "holding" cartridge.
Figure 10:
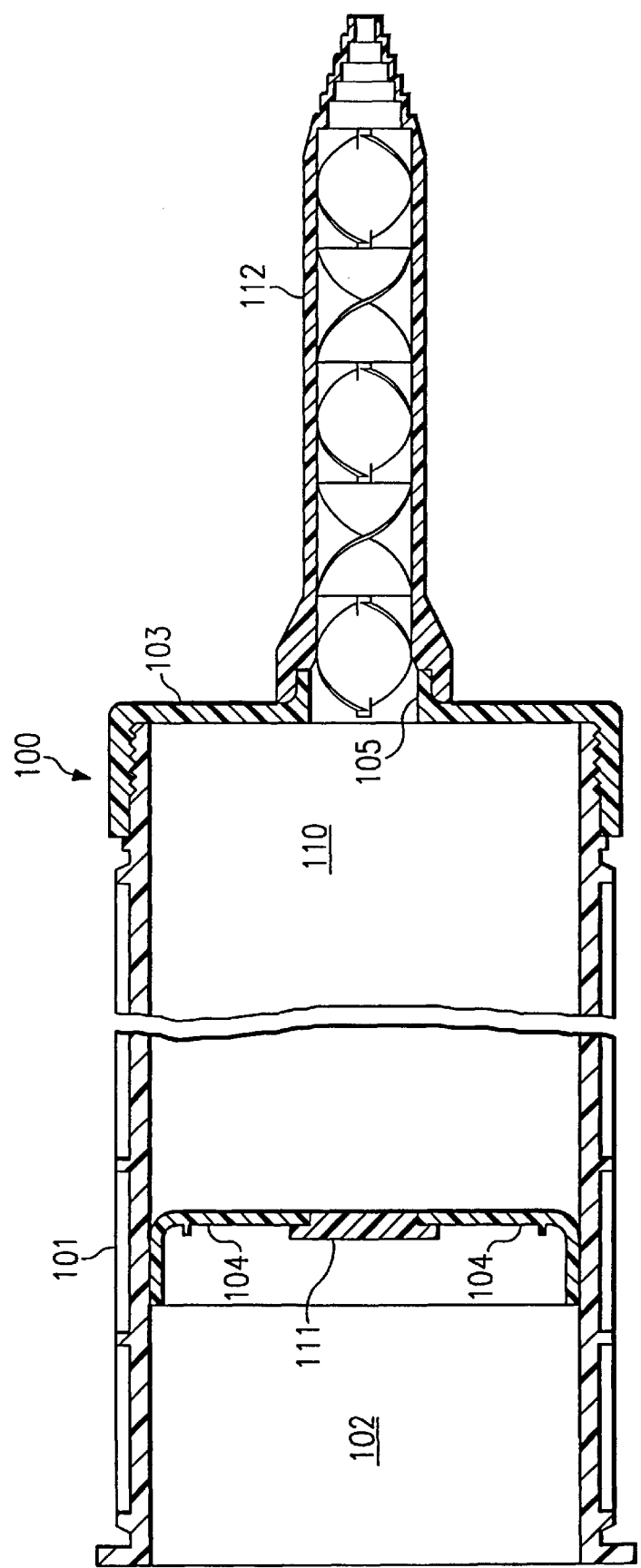
FIG. 10 is a cross-sectional view along the longitudinal axis of the filled "holding cartridge", with the outlet protector cap having been replaced by a static mixer, and the initial static mixer having been replaced by a protector cap.

Another way of achieving the desired partial polymerization prior to the injection of the bone cement into the bone site is the use of a "holding" cartridge 100, as illustrated in FIGS. 8–10. The "holding" cartridge 100 comprises an annular side wall 101 forming a cylindrical compartment 102 and having an externally threaded section at the outlet end thereof, an end cap 103 provided with matching internal threads so that the cap 103 can be secured to the outlet end of the annular side wall 102, and a piston 104 slidably positioned within the compartment. The end cap 103 has an opening therein which is defined by a longitudinally extending annular wall 105 and which is temporarily sealed by a plug 106. The piston 104 has a longitudinally extending flange 107 at its outer periphery extending away from the end cap 103, with the exterior surface of the flange 107 being in sliding contact with the internal surface of the compartment 102, whereby the piston 104 is maintained coaxially with the compartment 102. The piston 104 has a central opening therethrough, into which the outlet end of a static mixer 108 is releasably secured.

When it is desired to prepare the bone cement, a dual compartment container containing two bone cement components, such as the container 10 of FIG. 1, can be the source of the bone cement. As shown in FIG. 9, the protector cap 24 has been removed from the container 10, and the container 10 has been inserted through the open end of the holding container 100 such that the centrally located annular wall 15 of the container 10 entered and engaged with the inlet end of the static mixer 108. A dispensing device is utilized to press the pistons 43 and 47 towards the outlet end of container 10, thereby passing the bone cement components from chamber 46 and 50 into and through the static mixer 108. The mixture of bone cement components exiting the static mixer 108 enters the single holding chamber 110, which is formed as the piston 104 is forced away from the end cap 103. When all, or at least the desired amount of the bone cement components have been transferred from the dual compartment container 10 through the static mixer 108 into the holding chamber 110, the dual compartment container 10 and the static mixer 108 are removed from the holding cartridge 100, and the opening in the piston 104 is sealed with a plug 111. When the desired degree of polymerization of the monomer in the bone cement mixture in holding chamber 110 has occurred, the plug 106 is removed, and a static mixer 112 can be positioned with its inlet end in engagement with the annular wall 105, as illustrated in FIG. 10. The static mixer 112 can be similar or even identical to the static mixer 61 of FIG. 4. A dispensing mechanism is then used to press the piston 104, with the plug 111 in place, towards the cap end 103, forcing the partially polymerized bone cement through static mixer 112 and into the bone site. This apparatus provides the advantage that the physician is able to control the residence time of the bone cement in a holding vessel, without any significant exposure of the mixed bone cement components to air during the polymerization in the holding vessel. The second static mixer 112 can also provide greater uniformity of the injected bone cement. However, if the first mixer 108 provides the desired degree of mixing, the static mixer 112 can be replaced by an injection nozzle without mixing elements. Where the second static mixer 112 is employed, it can be shorter than would be necessary for the single static mixer of FIG. 4, thus reducing the resistance to flow of the partially polymerized bone cement therethrough.

While each of the two illustrated dual chamber containers is formed of a rigid material, it is within the scope of the invention to employ a flexible container having two separate chambers for containing the two liquid components. The flexible container can be formed of opposing layers of polyethylene film joined together along the longitudinal edge margins as well as along a longitudinal central portion, thereby forming two separate chambers. Such a flexible container can be provided with a rupturable wall separating the two chambers, so that upon rupturing the separating wall the two components can be mixed within the container. Similarly, a flexible container can be provided with a removable barrier between the two chambers, as in Magnusson et al, U.S. Pat. No. 5,370,221, such that upon removal of the barrier the two components can be mixed within the container. Such a flexible container can be provided with an outlet end which can be connected to the inlet of a suitable mixer, e.g., a static mixer-dispenser, a dynamic mixer, etc. At such outlet end of the container, the polyethylene films can be joined to a molded end wall structure, while the end of the container remote from the molded end wall structure can be formed by sealing together the opposing layers of the polyethylene film. The two liquid components could be simultaneously extruded from the separate chambers of the flexible container by subjecting the flexible container to progressive compression, e.g., by rolling up the flexible container beginning with the end thereof remote from the outlet of the container.

Suitable bone cement liquid monomers for use in the first and second liquid components are the free radical polymerizable methacrylic ester monomers which are liquid and which can be safely polymerized in a human body. The monomers having the generic formula $CH_2=C(CH_3)COOR$, wherein R is an alkyl radical having from 1 to 4 carbon atoms, are presently preferred, such that the monomer contains a total of 5 to 8 carbon atoms. Suitable examples include methyl methacrylate, ethyl methacrylate, isopropyl methacrylate, n-propyl methacrylate, isobutyl methacrylate, t-butyl methacrylate, and mixtures of any two or more thereof. In general, such methacrylic ester monomer(s) will be the sole monomeric ingredient of the bone cement; however, it is possible to include a minor amount of another suitable monomer such as styrene or an alkyl acrylate which will copolymerize readily with the methacrylic ester monomer. In such instances, the methacrylic ester monomer will generally constitute at least 75 weight percent, preferably at least 85 weight percent, and more preferably at least 95 weight percent of the total monomers.

Suitable bone cement polymer powders include any of the polymers of the above-described homopolymers and copolymers of methacrylic ester monomers having 5 to 8 carbon atoms. While the bone cement polymer powder can be a polymer of a free radical polymerizable monomer other than the specific liquid monomer being employed in the bone cement, it is presently preferred that the bone cement polymer powder be a polymer or copolymer of the same monomer or comonomers constituting the liquid monomeric ingredient(s) of the bone cement.

The first liquid component is formed by premixing a sufficient amount of a liquid methacrylic ester monomer with bone cement polymer powder and a polymerization initiator, preferably soluble in the monomer, to result in a liquid mixture. A stabilizer, preferably soluble in the monomer, is included in the first liquid component to prevent spontaneous polymerization of the monomer contained in the first liquid component. The polymerization initiator can be any suitable hydroperoxide, organic peroxide, or azo compound. Presently preferred initiators are the diacyl peroxides such as dibenzoyl peroxide, di-p-chlorobenzoyl peroxide, dilauroyl peroxide, dibenzoyl peroxide, etc., and combinations of any two or more thereof, with dibenzoyl peroxide being the most preferred initiator. Any suitable stabilizer can be employed, e.g., hydroquinone, t-butyl-p-cresol, a combination of hydroquinone and ascorbic acid, hydroxymethoxybenzophenone, etc., and mixtures of any two or more thereof.

The second liquid component is formed by premixing a sufficient amount of a liquid methacrylic ester monomer with bone cement polymer powder, if any, and an activator to result in a liquid mixture. A stabilizer, preferably soluble in the monomer, is included in the second liquid component to prevent spontaneous polymerization of the monomer contained in the second liquid component. While the specific liquid monomer employed in the second liquid component can be different from the specific liquid monomer employed in the first liquid component, it is preferred that they be the same. Similarly, while the specific polymer powder for the second liquid component can be different from the specific polymer powder of the first liquid component, it is preferred that they be the same. Any suitable activator can be employed, e.g., liquid N,N-dimethyl-p-toluidine (DMPT). However, it is presently preferred that the DMPT be replaced by a more biocompatible activator, for example, 4-N,N-(dimethylamino)phenethanol (DMAPE). Any suitable stabilizer can be employed, e.g., hydroquinone, t-butylp-cresol, a combination of hydroquinone and ascorbic acid, hydroxymethoxybenzophenone, etc., and mixtures of any two or more thereof.

The monomer/polymer ratio of each of the first and second liquid components can range upwardly from the minimum required for the respective component to be a liquid mixture to the maximum at which the desired final monomer/ratio can be achieved when the two liquid components are mixed together to form the unset bone cement. The amount of each of the first and second liquid components will be the amount necessary, with the given monomer/polymer ratio of each liquid component, to provide the desired amount of unset bone cement having the desired final monomer/polymer ratio, e.g., about 0.5 milliliter of monomer per gram of polymer powder.

The amount and type of activator and initiator should be selected to adjust the set-time of the resulting bone cement to be within the range of approximately 8 to approximately 10 minutes, when the two liquid components are mixed under air free conditions, as this would correspond to the normal set-time of many presently employed bone cements, thus avoiding any requirement for the operating room personnel to be accustomed to a different set-time. The poly (alkyl methacrylate) powder should be manufactured under high pressure to provide high molecular weight polymer having improved fracture toughness and fatigue characteristics. One of the liquid components can include a dye that would provide a visual indicator of the completeness of mixing. The resulting colored bone cement would also be valuable in revision surgery to distinguish between bone and cement. A radiopacifier, e.g., barium sulfate or zirconium dioxide, can also be included in one or both of the liquid bone cement components.

The total amount of monomer required in such two liquid components is probably less than required in conventional bone cement. Thus, the heat generated by the resulting exothermic polymerization during the setting of the resulting bone cement would be less. In the absence of oxygen to react with the benzoyl free radical, larger amounts of benzoyl free radicals are available to initiate polymerization of the monomer. Thus, because of the absence of oxygen, the amount of initiator required would be less than that of conventional bone cement.

EXAMPLE I

The delivery system of FIGS. 1–5 having two cylindrical chambers of equal diameter in a side-by-side configuration is utilized to package two liquid components, each having an equal volume and each comprising 20 grams of poly(methyl methacrylate) powder and 10 ml of methyl methacrylate monomer at a monomer/polymer ratio of 0.5 ml/gm. The first component also contains dibenzoyl peroxide as the polymerization initiator, and hydroquinone as the monomer stabilizer. The second liquid component also contains N,N-dimethyl-p-toluidine as the activator and hydroquinone as the monomer stabilizer. Upon mixing of the two liquid components and the extrusion of the mixture through the outlet nozzle section 66, the mixture would contain 40 grams of poly(methyl methacrylate) dispersed in 20 ml of methyl methacrylate monomer and would have an overall monomer/polymer ratio of 0.5 ml/gm.

EXAMPLE II

The delivery system of FIGS. 6–7 having two concentric chambers of different volumes is utilized to package two liquid components, the first liquid component being in the larger chamber 79 and comprising 80 grams of polymer and 30 ml of monomer, and the second liquid component being in the smaller chamber 87 and comprising 10 ml of monomer. The first liquid component also contains dibenzoyl peroxide as the polymerization initiator, and hydroquinone as the monomer stabilizer. The second liquid component also contains 4-N,N-(dimethylamino)phenethanol) as the activator and hydroquinone as the monomer stabilizer. Upon mixing and extrusion through the outlet nozzle section 66, the mixture would contain 80 grams of poly(methyl methacrylate) dispersed in 40 ml of methyl methacrylate monomer and would have an overall monomer/polymer ratio of 40 ml/80 gm, or 0.5 ml/gm.

Reasonable variations and modifications to the invention are possible within the scope of the foregoing disclosure and the appended claims to the invention.

That which is claimed is:

1. A system comprising:
   a drive member, which comprises:
      a first container, having a first end and a second end, including a first chamber and a second chamber located between the first end and the second end, each chamber having an outlet at the second end of the first container; and
      a component mixing device, having an outlet and an inlet, such inlet being in fluid communication with the respective outlets of the first chamber and the second chamber,
      whereas the first chamber is adapted to receive a first component and further receive a driving member to selectively decrease a volume of the first chamber and force a received first component through the outlet of the first chamber, and
      whereas the second chamber is adapted to receive a second component and further receive a driving member to selectively decrease a volume of the second chamber and force a received second component through the outlet of the second chamber; and
   a second container, having a first end and a second end with an outlet, to receive the drive member,
   wherein when the drive member is received by the second container, a third chamber is operatively formed between the drive member and the second end of the second container,
   wherein the third chamber is in fluid communication with the outlet of the first chamber and the outlet of the second chamber via the component mixing device, and
   wherein application of a sufficient force to the drive member can effect a discharge of mixture of a first component and a second component, once received within the third chamber, through the outlet of the second container.

2. A system in accordance with claim 1, wherein the component mixing device is a static mixer.

3. A system in accordance with claim 2, wherein a physical configuration of the path prevents significant quantities of air from being introduced into a mixture of the first component and the second component during their combination therethrough.

4. A system in accordance with claim 1, wherein the component mixing device is a static mixer that includes a plurality of misaligned, substantially spiral mixing vanes, whereas each mixing vane effects a division of a received fluid flow within the component mixing device.

5. A system in accordance with claim 1, further comprising a seal extending across the outlet of the first chamber and the outlet of the second chamber to prevent an introduction of at least air into the first chamber and the second chamber, wherein the seal may be disrupted upon the first component or the second component being forced from the respective first chamber or the second chamber.

6. A system in accordance with claim 1, wherein the first chamber and the second chamber are independent.

7. A fluid mixture preparation system comprising:
a first fluid source, including a first movable drive member to drive a first fluid therefrom;
a second fluid source, including a second movable drive member to drive a second fluid therefrom;
a fluid mixer having an inlet and an outlet, wherein the inlet is adapted to receive both a first fluid from the first fluid source and a second fluid from the second fluid source; and
a container having a first end, a second end with an outlet, and a third driving member received within the container to form a chamber between the third driving member and the second end, wherein the chamber is in fluid communication with the outlet of the fluid mixer.

8. A fluid mixture preparation system in accordance with claim 7, wherein the fluid mixer is a static mixer having a path defined therethrough.

9. A fluid mixture preparation system in accordance with claim 8, wherein a physical configuration of the path prevents significant quantities of air from being introduced into a combination of the first fluid and the second fluid during mixing.

10. A fluid mixture preparation system in accordance with claim 7, wherein the outlet of the fluid mixer is in fluid communication with the chamber through an orifice which extends through the driving member received within the container.

11. A fluid mixture dispensing system for providing a liquid bone cement having a first monomer/polymer ratio, the system comprising:
a first container having a first end and a second end, the container having a first compartment and a second compartment located between the first and second ends, each of the first and second compartments having a longitudinal axis, each of the first and second compartments having an outlet in the second end of the container, the container being free of internal communication between the first compartment and the second compartment;
a first piston positioned in the first compartment to form a first chamber between the first piston and the outlet of the first compartment, wherein the first chamber contains a first liquid component for the liquid bone cement, the first liquid component comprising a liquid alkyl methacrylate, a polymerization initiator, a stabilizer for preventing spontaneous polymerization of the liquid alkyl methacrylate in the first liquid component, and poly(alkyl methacrylate);
a second piston positioned in the second compartment to form a second chamber between the second piston and the outlet of the second compartment, wherein the second chamber contains a second liquid component for the liquid bone cement, the second liquid component comprising a liquid alkyl methacrylate, an activator, and a stabilizer for preventing spontaneous polymerization of the liquid alkyl methacrylate in the second liquid component;
a second container having a first end, a second end with an outlet, and a piston positioned in the second container to form a holding chamber between the piston and the second end to enable at least partial polymerization of a first liquid component-second liquid component mixture, wherein the third chamber is in fluid communication with each outlet of the first chamber and the second chamber via a component mixer; and
said component mixer, having an outlet and an inlet, and the component mixing device inlet is in fluid communication with the respective outlets of the first compartment and the second compartment.

12. A fluid mixture dispensing system in accordance with claim 11, further comprising a seal extending across the outlets of the first and the second compartments to prevent an introduction of at least air into the first compartment and the second compartment, wherein the seal may be disrupted upon the first liquid component or the second liquid component being forced from the respective first compartment or the second compartment.

13. A fluid mixture dispensing system in accordance with claim 11, wherein the outlet of the first compartment and the outlet of the second compartment are in fluid communication with the third chamber through an orifice which extends through the piston of the second container.

14. A fluid mixture dispensing system in accordance with claim 11, wherein the liquid alkyl methacrylate present in the first liquid component is an amount which is at least sufficient to provide the first liquid component as a liquid mixture.

15. A fluid mixture dispensing system in accordance with claim 14, wherein the first chamber is substantially air free.

16. A fluid mixture dispensing system in accordance with claim 11, wherein the liquid alkyl methacrylate present in the second liquid component is an amount which is at least sufficient to provide the second liquid component as a liquid mixture.

17. A fluid mixture dispensing system in accordance with claim 16, wherein the second chamber is substantially air free.

18. A fluid mixture dispensing system in accordance with claim 11,
wherein the liquid alkyl methacrylate in the first liquid component comprises liquid methyl methacrylate;
wherein the poly(alkyl methacrylate) in the first liquid component comprises poly(methyl methacrylate) which was in powder form prior to inclusion in the first liquid component;
wherein liquid alkyl methacrylate and poly(alkyl methacrylate) are present in the first liquid component at a second monomer/polymer ratio;
wherein the liquid alkyl methacrylate in the second liquid component comprises liquid methyl methacrylate;
wherein the second liquid component further comprises poly(methyl methacrylate) which was in powder form prior to inclusion in the second liquid component;
wherein liquid alkyl methacrylate and poly(alkyl methacrylate) are present in the second liquid component at a third monomer/polymer ratio; and
wherein when the first and second liquid components are mixed together to produce a liquid bone cement, the second and third monomer/polymer ratios will result in the thus produced liquid bone cement having the first monomer/polymer ratio.

19. A fluid mixture preparation system comprising:
a first container, having an outlet and a first movable drive member, to receive a first fluid component;
a second container, having an outlet and a second movable drive member, to receive a second fluid component;

a third container having an inlet and an outlet, the inlet of the third container being in fluid communication with both the outlet of the first container and the outlet of the second container via a static mixer;

a driver, received by the third container, to drive a fluid mixture received within the third container through the outlet of the third container; and said static mixer, positioned between the outlets of the first container and the second container and the third container, wherein the fluid mixture operatively includes a portion of the first fluid component and a portion of the second fluid component.

20. A fluid mixture preparation system comprising:

a first container, having an outlet and a first movable drive member, to receive a first fluid component;

a second container, having an outlet and a second movable drive member, to receive a second fluid component;

a third container having an inlet and an outlet, the inlet of the third container being in fluid communication with both the outlet of the first container and the outlet of the second container;

a driver, received by the third container, to drive a fluid mixture received within the third container through the outlet of the third container; and a static mixer, positioned downstream from the third container, whereas a fluid mixture driven from the third container passes through the static mixer and is mixed prior to being dispensed from the fluid mixture preparation system, wherein the fluid mixture operatively includes a portion of the first fluid component and a portion of the second fluid component.

* * * * *